US010947508B2

(12) United States Patent
Jin et al.

(10) Patent No.: US 10,947,508 B2
(45) Date of Patent: Mar. 16, 2021

(54) CULTURE MEDIUM FOR MESENCHYMAL STEM CELLS (71) Applicants: AJINOMOTO CO., INC., Tokyo (JP); Kyoto University, Kyoto (JP)

(72) Inventors: Yonghui Jin, Kyoto (JP); Ikue Harata, Kawasaki (JP); Sho Senda, Kawasaki (JP); Hiroki Ozawa, Kawasaki (JP); Tsuyoshi Kobayashi, Kawasaki (JP); Junya Toguchida, Kyoto (JP); Makoto Ikeya, Kyoto (JP)

(73) Assignees: AJINOMOTO CO., INC., Tokyo (JP); Kyoto University, Kyoto (JP)

(*) Notice: Subject to any disclaimer, the term of this patent is extended or adjusted under 35 U.S.C. 154(b) by 59 days.

(21) Appl. No.: 15/435,705

(22) Filed: Feb. 17, 2017

(65) Prior Publication Data
US 2017/0198258 A1    Jul. 13, 2017

Related U.S. Application Data (63) Continuation of application No. PCT/JP2015/073349, filed on Aug. 20, 2015.

(30) Foreign Application Priority Data

Aug. 21, 2014   (JP) .............................. JP2014-168580

(51) Int. Cl.
*C12N 5/0775* (2010.01)
*C12N 5/00* (2006.01)
*A61K 35/55* (2015.01)
*A61K 35/56* (2015.01)
*A61K 35/28* (2015.01)
*A61K 35/12* (2015.01)

(52) U.S. Cl.
CPC ............ *C12N 5/0663* (2013.01); *A61K 35/28* (2013.01); *A61K 35/55* (2013.01); *A61K 35/56* (2013.01); *C12N 5/00* (2013.01); *A61K 2035/124* (2013.01); *C12N 2500/32* (2013.01); *C12N 2500/84* (2013.01)

(58) Field of Classification Search
None
See application file for complete search history.

(56) References Cited

U.S. PATENT DOCUMENTS

| 4,211,766 A * | 7/1980 | Bjorklund .......... A61K 39/0011 424/184.1 |
|---|---|---|
| 9,321,995 B2 | 4/2016 | Liu et al. |
| 2010/0261276 A1 | 10/2010 | Park et al. |
| 2013/0164849 A1 | 6/2013 | Ra et al. |
| 2013/0252335 A1 | 9/2013 | Kume et al. |
| 2014/0178987 A1 | 6/2014 | Liu et al. |
| 2014/0322811 A1 | 10/2014 | Kang et al. |
| 2014/0370600 A1 | 12/2014 | Suh et al. |

FOREIGN PATENT DOCUMENTS

| CN | 101984048 A | 3/2011 |
|---|---|---|
| CN | 103060264 A | 4/2013 |
| CN | 103146755 A | 6/2013 |
| EP | 2 083 071 A1 | 7/2009 |
| EP | 2 752 48 A1 | 7/2014 |
| JP | 2006-325445 A | 12/2006 |
| JP | 2009-100702 A | 5/2009 |
| JP | 2013-530721 A | 8/2013 |
| WO | WO 2008/049281 A1 | 5/2008 |
| WO | WO 2009/014272 A1 | 1/2009 |
| WO | WO 2012/056997 A1 | 5/2012 |
| WO | WO 2013/032052 A1 | 3/2013 |
| WO | WO 2013/081436 A1 | 6/2013 |

OTHER PUBLICATIONS

Current Protocols in Protein Science, Desalting, Concentration, and Buffer Exchange by Dialysis and Ultrafiltration, Unit 4.4, 2001, John Wiley & Sons, Inc., retrieved from the internet: http://groups.molbiosci.northwestern.edu/morimoto/research/Protocols/II.%20Eukaryotes/A.%20Cell%20Culture/2c.%20Dialysis%20of%20.*
Aldahmash et al., Human serum is as efficient as fetal bovine serum in supporting proliferation and differentiation of human multipotent stromal (mesenchymal) stem cells in vitro and in vivo, Stem Cell Rev, Nov. 2011; 7(4):860-868.*
Barngrover et al., J. Cell Sci. 78, pp. 173-189 (1985).*
HiMedia Product Information: Leibovitz's L-15 Medium, retrieved from the internet: http://groups.molbiosci.northwestern.edu/morimoto/research/Protocols/II.%20Eukaryotes/A.%20Cell%20Culture/2c.%20Dialysis%20of%20FBS.pdf.*
Ong et al., Nature Protocols, vol. 1, No. 6, 2006, pp. 2650-2660.*
Rocha et al., Journal of Proteome Research, 2014, vol. 13, pp. 1045-1054.*
Bieback et al, Stem Cells Translational and Clinical Research, 2009; 27:2331-2341. (Year: 2009).*
Elmore et al, In Vitro, 1977; 13(12):837-842. (Year: 1977).*
Freshney, R Ian, editor. "Media." Culture of Animal Cells a Manual of Basic Technique, 4th ed., Wiley-Liss, 1994, pp. 94-104. (Year: 1994).*
Lodish H, Berk A, Zipursky SL, et al. Molecular Cell Biology. 4th edition. New York: W. H. Freeman; 2000. Section 6.1, Growth of Microorganisms in Culture. Available from: https://www.ncbi.nlm.nih.gov/books/NBK21593/ (Year: 2000).*
Extended European Search Report dated Mar. 19, 2018 in European Patent Application No. 15833662.8, 9 pages.
Kyung-Min Choi, et al., "Effect of essential and nonessential amino acid compositions on the in vitro behavior of human mesenchymal stem cells", Korean Journal of Chemical Engineering, vol. 24., No. 6, 2007,pp. 1058-1063.

(Continued)

*Primary Examiner* — Allison M Fox
(74) *Attorney, Agent, or Firm* — Oblon, McClelland, Maier & Neustadt, L.L.P.

(57) ABSTRACT

Mesenchymal stem cells may be culture for a long period, without using any special apparatus, equipment and the like, in a medium in which seven kinds of nonessential amino acids of glycine, alanine, serine, proline, asparagine, aspartic acid, and glutamic acid are reduced.

10 Claims, 4 Drawing Sheets

(56) References Cited

OTHER PUBLICATIONS

Gustavo A. Higuera, Ph.D., et al., "Patterns of Amino Acid Metabolism by Proliferating Human Mesenchymal Stem Cells", Tissue Engineering: Part A, vol. 18, No. 5-6, 2012, pp. 654-664.
Yonghui Jin, et al., "Mesenchymal stem cells cultured under hypoxia escape from senescence via down-regulation of p16 and extracellular signal regulated kinase", Biochemical and Biophysical Research Communications, vol. 391, 2010, pp. 1471-1476.
Y. M. Elhassan, et al., Theriogenology, vol. 55, p. 1907-1918 (2001).
J.A. Lawitts., et al., Methods in Enzymology, vol. 225, pp. 153-164 (1993).

\* cited by examiner

TG: neutral fat (triglyceride)

FIG. 5B

TG: neutral fat (triglyceride)

CULTURE MEDIUM FOR MESENCHYMAL STEM CELLS

CROSS REFERENCES TO RELATED APPLICATIONS

This application is a continuation of International Patent Application No. PCT/JP2015/073349, filed on Aug. 20, 2015, and claims priority to Japanese Patent Application No. 2014-168580, filed on Aug. 21, 2014, both of which are incorporated herein by reference in their entireties.

BACKGROUND OF THE INVENTION

Field of the Invention

The present invention relates to media for mesenchymal stem cells, a culture method of mesenchymal stem cells, and the like.

Discussion of the Background

Mesenchymal stem cells (MSC) are one type of somatic stem cells present in the bone marrow and the like of adult, and are defined as an adherent cell having an ability to differentiate into bone, cartilage or adipocyte. Unlike embryonal stem cells such as embryonic stem (ES) cells, induced pluripotent stem (iPS) cell and the like, (MSC) are considered to have an extremely low risk of canceration, and considered to be highly promising as a cellular material to be used for regenerative medicine. Also in Japan, plural clinical studies are already ongoing mainly on articular diseases.

Mesenchymal stem cells are generally known as cells that become "senescent", and it is known that a long culture period (increased number of division) causes low proliferation speed, and further, termination (see Jin, Y., et al., Biochem Biophys Res Commun., Vol. 391, p. 1471-1476, which is incorporated herein by reference in its entirety). Jin, Y., et al., Biochem Biophys Res Commun., Vol. 391, p. 1471-1476 reports that senescence of human mesenchymal stem cells (hMSC) can be suppressed by culturing under hypoxic conditions. However, it is completely unknown how the composition of amino acids in the medium influences senescence and proliferation of human mesenchymal stem cells.

JP-A-2009-100702 and WO 2012/056997A1, both of which are incorporated herein by reference in their entireties, disclose examples of stem cell culture techniques by removal of particular amino acids from the medium. These are techniques relating to pluripotent stem cells such as ES cell and iPS cell, in which undifferentiated cells remaining after differentiation induction are selectively killed and removed to increase purity of the differentiated cells in the cell composition. To date, there are no known cases where removal of particular amino acids from the medium suppresses cell senescence or promotes proliferation in any stem cells, regardless of whether it is a somatic stem cell or a pluripotent stem cell.

Mesenchymal stem cells become senescent, and it is known that a long culture period (increased number of division) causes low proliferation speed, and further, termination. Therefore, it is not easy to secure a sufficient number of cells, which forms one obstacle to the basic research and clinical application of human mesenchymal stem cells.

SUMMARY OF THE INVENTION

Accordingly, it is one object of the present invention to provide novel means for growing mesenchymal stem cells particularly, human mesenchymal stem cells, for a longer period than before, without using special apparatus, equipment and the like.

In particular, it is an object of the present invention to provide novel culture media for culturing mesenchymal stem cells.

It is another object of the present invention to provide novel methods of culturing mesenchymal stem cells.

It is another object of the present invention to provide novel cultures of mesenchymal stem cells.

These and other objects, which will become apparent during the following detailed description, have been achieved by the inventors' discovery that when human mesenchymal stem cells are cultured in a culture medium containing reduced amounts of seven kinds of non-essential amino acids of glycine, alanine, serine, proline, asparagine, aspartic acid, and glutamic acid, the human mesenchymal stem cells can be growing cultured for a longer period than when cultured in a conventional culture medium free of reduction of the amounts of the non-essential amino acids, and more mesenchymal stem cells can be obtained.

Thus, the present provides the following:

(1) A medium for mesenchymal stem cells, comprising at least one kind of amino acid, wherein a concentration thereof is: glycine less than 5 μM, alanine less than 5 μM, serine less than 3 μM, proline less than 5 μM, asparagine less than 1 μM, aspartic acid less than 2 μM, and/or glutamic acid less than 3 μM.

(2) The medium of the above-mentioned (1), comprising less than 5 μM of glycine.

(3) The medium of the above-mentioned (1), comprising less than 1 μM of glycine.

(4) The medium of any of the above-mentioned (1) to (3), comprising less than 5 μM of alanine.

(5) The medium of any of the above-mentioned (1) to (3), comprising less than 1 μM of alanine.

(6) The medium of any of the above-mentioned (1) to (5), comprising less than 3 μM of serine.

(7) The medium of any of the above-mentioned (1) to (5), comprising less than 0.7 μM of serine.

(8) The medium of any of the above-mentioned (1) to (7), comprising less than 5 μM of proline.

(9) The medium of any of the above-mentioned (1) to (7), comprising less than 1 μM of proline.

(10) The medium of any of the above-mentioned (1) to (9), comprising less than 1 μM of asparagine.

(11) The medium of any of the above-mentioned (1) to (9), comprising less than 0.1 μM of asparagine.

(12) The medium of any of the above-mentioned (1) to (11), comprising less than 2 μM of aspartic acid.

(13) The medium of any of the above-mentioned (1) to (11), comprising less than 0.5 μM of aspartic acid.

(14) The medium of any of the above-mentioned (1) to (13), comprising less than 3 μM of glutamic acid.

(15) The medium of any of the above-mentioned (1) to (13), comprising less than 0.7 μM of glutamic acid.

(16) The medium of the above-mentioned (1), comprising less than 5 μM of glycine, less than 5 μM of alanine, less than 3 μM of serine, less than 5 μM of proline, less than 1 μM of asparagine, less than 2 μM of aspartic acid, and less than 3 μM of glutamic acid.

(17) The medium of the above-mentioned (1), comprising less than 1 μM of glycine, less than 1 μM of alanine, less than 0.7 μM of serine, less than 1 μM of proline, less than 0.1 μM of asparagine, less than 0.5 μM of aspartic acid, and less than 0.7 μM, of glutamic acid.

(18) The medium of any of the above-mentioned (1) to (17), comprising a serum or serum replacement subjected to a low molecule removal treatment.

(19) The medium of the above-mentioned (18), wherein the aforementioned low molecule removal treatment is performed by dialysis.

(20) The medium of the above-mentioned (18) or (19), wherein the serum is a human serum.

(21) The medium of any of the above-mentioned (1) to (20), which is free of a component derived from a non-human animal.

(22) The medium of any of the above-mentioned (1) to (21), wherein the mesenchymal stem cell is a human mesenchymal stem cell.

(23) The medium of the above-mentioned (22), wherein the mesenchymal stem cell is collected from bone marrow.

(24) A method of culturing a mesenchymal stem cell, comprising a step of culturing a mesenchymal stem cell in the medium of any of the above-mentioned (1) to (23).

(25) The culture method of the above-mentioned (24), wherein the step of culturing the mesenchymal stem cell is a step of growing a mesenchymal stem cell for not less than 70 days.

(26) A cell composition obtained by the culture method of the above-mentioned (24) or (25).

(27) The cell composition of the above-mentioned (26), which is positive to at least one marker selected from the group consisting of CD73, CD90 and CD105.

(28) The cell composition of the above-mentioned (26), which is positive to at least one marker selected from the group consisting of CD73, CD90 and CD105, and negative to CD45, CD34, CD14, CD11b, CD79, CD19 and HLA-DR.

(29) A cell for cell medicine, which is obtained by the culture method of the above-mentioned (24) or (25).

(30) A medium for mesenchymal stem cells, not comprising glycine, alanine, serine, proline, asparagine, aspartic acid and glutamic acid but comprising a serum or serum replacement subjected to a low molecule removal treatment.

(31) The medium of the above-mentioned (30), comprising histidine, isoleucine, leucine, lysine, methionine, phenylalanine, threonine, tryptophan, and valine.

(32) The medium of the above-mentioned (31), further comprising arginine, cysteine, glutamine, and tyrosine.

Effect of the Invention

According to the present invention, mesenchymal stem cells can be cultured over a long period, which has been difficult to achieve heretofore. Therefore, more mesenchymal stem cells can be conveniently obtained and mesenchymal stem cells can be supplied in a large amount for use in the research, medical treatment and the like.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

The present invention provides a medium for mesenchymal stem cells, containing a reduced amount of at least one kind of amino acid selected from the group consisting of amino acids of glycine, alanine, serine, proline, asparagine, aspartic acid and glutamic acid (hereinafter sometimes to be abbreviated as "the medium of the present invention"). More specifically, a medium for mesenchymal stem cells, wherein a concentration of at least one kind of amino acid is: glycine less than 5 µM, alanine less than 5 µM, serine less than 3 µM, proline less than 5 µM, asparagine less than 1 µM, aspartic acid less than 2 µM, and/or glutamic acid less than 3 µM, is provided.

The amino acids described in the present specification mean any of L-form, D-form, and DL-form, and mean not only a free form of each amino acid but also a salt form.

Examples of the salt form include an acid addition salt, a salt with a base and the like, and a salt not showing cytotoxicity and acceptable as a pharmaceutical product is preferable. Examples of the acid forming such salt include inorganic acids such as hydrogen chloride, hydrogen bromide, sulfuric acid, phosphoric acid and the like, and organic acids such as acetic acid, lactic acid, citric acid, tartaric acid, maleic acid, fumaric acid, monomethylsulfuric acid and the like. Examples of the base forming such salt include hydroxide or carbonate of a metal such as sodium, potassium, calcium and the like, inorganic bases such as ammonia and the like, organic base such as ethylenediamine, propylenediamine, ethanolamine, monoalkylethanolamine, dialkylethanolamine, diethanolamine, triethanolamine and the like. The above-mentioned salt may be a hydrate (hydrate salt).

In the medium of the present invention, the amount of at least one kind of amino acid selected from the group consisting of glycine, alanine, serine, proline, asparagine, aspartic acid and glutamic acid (hereinafter these 7 kinds of amino acid are sometimes to be collectively referred to as "reduced amino acid of the present invention"). In the present specification, "reduced" means that the amount is smaller than that used for a general medium, and that the content thereof is kept low to a level that enables growth of mesenchymal stem cells for a long period. Examples of the amount used for a general medium include glycine 133 to 667 µM, alanine 50 to 400 µM, serine 238 to 400 µM, proline 150 to 400 µM, asparagine 50 to 400 µM, aspartic acid 50 to 400 µM, and glutamic acid 50 to 510 µM. To realize the reduction of the amount of amino acid, the basal medium used for preparing the medium of the present invention and additives to be added thereto are preferably those free of the reduced amino acid of the present invention or those subjected to an operation to remove small molecules such as the reduced amino acid of the present invention and the like. In a preferable embodiment, the medium of the present invention is substantially free of at least one kind, more preferably all 7 kinds, of the reduced amino acid of the present invention. Being "substantially free of" means that a basal medium and additives thereof, which are free of the reduced amino acid of the present invention or those subjected to an operation to remove small molecules such as the reduced amino acid of the present invention, are used, whereby the final concentration of the reduced amino acid of the present invention during culture in the medium of the present invention is kept as low as possible, preferably the concentration in the medium of the present invention is below the detection limit. The amino acid can be detected by an amino acid analysis method by a ninhydrin method (see e.g., Clinical Chemistry (1997), Vol. 43, No. 8, p 1421-1428, which is incorporated herein by reference in its entirety) and the like. When a ninhydrin method is used as a detection method of amino acid, the "concentration below the detection limit" means a concentration of the level at which detection by the amino acid analysis method by a ninhydrin method is not possible. Specific examples of the concentration of each amino acid in the reduced amino acid of the present invention include glycine less than 5 µM, preferably less than 1 µM, more preferably less than 0.8 µM, alanine less than 5 µM, preferably less than 1 µM, more preferably less than 0.8 µM, serine less than 3 µM, preferably less than 0.7 µM, more preferably less than 0.4 µM, proline less than 5 µM, preferably less than 1 µM, more preferably less than 0.7 µM, asparagine less than 1 µM, preferably less than 0.1 µM, more preferably less than 0.06 µM, aspartic acid less than 2 µM, preferably less than 0.5 µM, more preferably less than 0.15 µM, glutamic acid less than 3 µM, preferably less than 0.7 µM, more preferably less than 0.5 µM.

In the medium of the present invention, the amount(s) of 1, 2, 3, 4, 5, 6, or 7 kinds of the 7 kinds of the reduced amino acid of the present invention is(are) reduced. When the amounts of plural kinds of amino acids are reduced, any amino acids may be combined. In a preferable embodiment, the amounts of all 7 kinds of the amino acid are reduced in the medium of the present invention.

The content of the amino acid other than the reduced amino acid of the present invention in the medium of the present invention is not particularly limited as long as it does not inhibit growth of mesenchymal stem cells, and a concentration used for a general cell culture can be appropriately adopted.

As the medium of the present invention, a basal medium known per se can be used, and the medium is not particularly limited as long as it does not inhibit the growth of mesenchymal stem cells. Examples thereof include DMEM, EMEM, IMDM (Iscove's Modified Dulbecco's Medium), GMEM (Glasgow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, Leibovitz's L-15, RITC80-7, MCDB105, MCDB107, MCDB131, MCDB153, MCDB201, NCTC109, NCTC135, Waymouth's MB752/1, CMRL-1066, Williams' medium E, Brinster's BMOC-3 Medium, E8 medium (see Nature Methods, 2011, 8, 424-429, which is incorporated herein by reference in its entirety), ReproFF2 medium (ReproCELL Incorporated), and a mixed medium thereof and the like. Also, a medium modified for mesenchymal stem cell culture, a mixture of the above-mentioned basal medium and other medium, and the like may be used. When desired, an operation to remove low molecular weight substances such as the reduced amino acids of the present invention may be applied to these media.

The medium of the present invention can contain an additive known per se. The additive is not particularly limited as long as it does not inhibit growth of mesenchymal stem cells and, for example, growth factor (e.g., insulin etc.), iron source (e.g., transferrin etc.), polyamines (e.g., putrescine etc.), mineral (e.g., sodium selenate etc.), saccharides (e.g., glucose etc.), organic acid (e.g., pyruvic acid, lactic acid etc.), amino acid other than the reduced amino acid of the present invention (e.g., L-glutamine etc.), reducing agent (e.g., 2-mercaptoethanol etc.), vitamins (e.g., ascorbic acid, d-biotin etc.), steroid (e.g., β-estradiol, progesterone etc.), antibiotic (e.g., streptomycin, penicillin, gentamicin etc.), buffering agent (e.g., HEPES etc.) and the like, lipids (e.g., linoleic acid etc.), and nucleic acids (e.g., thymidine etc.). In addition, additives known per se, which have conventionally been used for the culture of mesenchymal stem cells can also be contained as appropriate. The additives are each preferably contained within a concentration range known per se.

The medium of the present invention may contain a serum. The serum is not particularly limited as long as it is derived from an animal and does not inhibit the growth of mesenchymal stem cells. Preferred is a mammal-derived serum (e.g., fetal bovine serum, human serum etc.), more preferred is a human serum. The concentration of the serum may be any as long as it is within a concentration range known per se. Furthermore, when a mesenchymal stem cell after culture is used for medical purposes, a serum-free medium can also be preferably used, since a component derived from other animal may be a blood-mediated pathogen or a xenoantigen. When serum is not contained, a replacement additive of serum (e.g., Knockout Serum Replacement (KSR) (Invitrogen), Chemically-defined Lipid concentrated (Gibco) etc.) may also be used. The above-mentioned serum and serum alternative additive are preferably free of the reduced amino acid of the present invention, or after an operation to remove low molecules such as the reduced amino acid of the present invention and the like.

That is, one embodiment of the medium of the present invention is "a medium for mesenchymal stem cells not added the reduced amino acid of the present invention and containing a serum or serum replacement subjected to a low molecule removal treatment". When desired, the medium may contain or preferably contains amino acid other than the reduced amino acid of the present invention, specifically, histidine, isoleucine, leucine, lysine, methionine, phenylalanine, threonine, tryptophan and valine. When desired, moreover, the medium may contain or preferably contains arginine, cysteine, glutamine and tyrosine.

When mesenchymal stem cells cultured in the medium of the present invention are used for medical purposes such as cell medicine and the like, the medium of the present invention more preferably is free of a component derived from a non-human animal, in view of the possibility of causing infection with pathogenic bacteria or becoming a xenoantigen.

The above-mentioned "operation to remove low molecules such as reduced amino acid of the present invention and the like" may be performed by any method as long as the reduced amino acid of the present invention can be removed while maintaining the desired effect of the sample to be subjected to the operation, and operations such as dialysis, gel filtration and the like can be mentioned. Specific examples include a method comprising adding amino acid other than the reduced amino acid of the present invention at a concentration necessary for the growth of mesenchymal stem cells to a reagent used for preparing a medium and containing medium ingredients (salts, vitamins, etc.) other than amino acid, and further adding a serum etc. after removal of the reduced amino acid of the present invention and other low molecules by an operation such as dialysis, gel filtration and the like.

The "stem cell" means an immature cell having self-renewal capacity and differentiation/growth capacity. The stem cell includes subpopulation such as pluripotent stem cell, multipotent stem cell, unipotent stem cell and the like, according to the differentiation potency. The pluripotent stem cell means a cell capable of differentiating into any tissue or cell constituting living organisms. The multipotent stem cell means a cell capable of differentiating into plural, though not all, kinds of tissues and cells. The unipotent stem cell means a cell capable of differentiating into specific tissues and cells.

The mesenchymal stem cell of interest in the present invention is one kind of multipotent stem cell which can differentiate into adipocyte, osteocyte, chondrocyte, muscle cell, hepatocyte, nerve cell, and the like, is different from pluripotent stem cells such as ES cell and iPS cell, and is known as a cell having a low possibility of forming a tumor when transplanted into a living body. The mesenchymal stem cell in the present invention can be mesenchymal stem cells collected from the bone marrow, preferably positive to one or more mesenchymal stem cell markers (e.g., CD73, CD90, CD 105, etc), more preferably said marker-positive, with expression of the molecule showing no expression in mesenchymal stem cell being negative. Examples of the molecule showing no expression in mesenchymal stem cell include CD45, CD34, CD14, CD11b, CD79, CD19, HLA-DR and the like.

The medium of the present invention can be preferably used for growth of mesenchymal stem cells derived from any animal. The mesenchymal stem cells cultured by using the medium of the present invention are, for example, mesenchymal stem cells derived from rodents such as mouse, rat, hamster, guinea pig and the like, Lagomorpha such as rabbit and the like, Ungulata such as swine, bovine, goat, horse, sheep and the like, Carnivora such as dog, cat and the like, primates such as human, monkey, Macaca mulatta, marmoset, orangutan, chimpanzee and the like. Preferred are mesenchymal stem cells derived from human.

The medium of the present invention is preferably a medium for growth culture of mesenchymal stem cells. The "medium for growth culture" is a medium which enables replication (i.e., growth) of the mesenchymal stem cell while maintaining the self replication ability and differentiation capacity of the mesenchymal stem cell. Therefore, mesenchymal stem cells cultured by the medium of the present invention are characterized in that they maintain proliferative capacity. In the present specification, the "proliferative capacity" means that the ability to perform cell division is not lost by cellular senescence and the like. When, for example, most of the cells in the culture (e.g., 60%, preferably 70%, more preferably 80%, further preferably 90%, most preferably 100% of the cells in the cell composition), are negative to cell senescence marker (e.g., increase in senescence-associated β-galactosidase activity etc.), and when the majority of the cells in the culture (e.g., 60%, preferably 70%, more preferably 80%, further preferably 90%, most preferably 100% of the cells in the cell composition) belong to any of G1, S, G2 or M phase of the cell cycle, the cells can be said to maintain proliferative capacity.

According to the medium of the present invention, mesenchymal stem cells can be efficiently cultured for a long period while maintaining the proliferative capacity. For example, mesenchymal stem cells can be cultured in the medium of the present invention while maintaining the proliferative capacity, for 50 days or more, preferably 70 days or more, more preferably 87 days or more, and further preferably 118 days or more. According to the medium of the present invention, since the proliferative capacity of mesenchymal stem cells is not lost, a large amount of mesenchymal stem cells can be obtained by culturing. A large amount of mesenchymal stem cells can be obtained by using the medium of the present invention as compared to the conventional method, and for example, mesenchymal stem cells in the number 1230 times or more greater than that at the start of the culture can be obtained.

Mesenchymal stem cells cultured in the medium of the present invention have the same level of ability to differentiate into osteocytes as compared to mesenchymal stem cells cultured in a conventional medium. Differentiation into osteocytes can be performed, for example, by culturing mesenchymal stem cells in a bone differentiation induction medium (e.g., DMEM medium added with 10(v/v) % FBS, 100 nM dexamethasone, 50 μM L-ascorbic acid-2 phosphate, 10 mM β-glycerophosphate). Whether the cell has differentiated into osteocyte can be confirmed by detecting the deposition of calcium ion in bone tissue by Arizalin Red staining. The mesenchymal stem cells cultured in the medium of the present invention have the same level of ability to differentiate into chondrocytes as compared to mesenchymal stem cells cultured in a conventional medium. Differentiation into chondrocytes can be performed, for example, by using a cartilage differentiation kit (Lonza: PT-3003) added with 10 ng/mL TGF-β3. Whether the cell has differentiated into chondrocytes can be confirmed, for example, by detecting production of glucosaminoglycan by a commercially available glucosaminoglycan assay kit and the like. The mesenchymal stem cells cultured in the medium of the present invention can have more promoted ability to differentiate into adipocytes as compared to mesenchymal stem cells cultured in a conventional medium. The cells can be differentiated into adipocytes by culturing mesenchymal stem cells in, for example, a adipose differentiation induction medium (e.g., high glucose-containing DMEM medium added with 10(v/v) % FBS, 0.01 mg/mL insulin, 1 μM dexamethasone, 0.2 mM indomethacin, 0.5 mM isobutylmethylxanthine). Whether the cell has differentiated into adipocyte can be confirmed, for example, by detecting production of triglyceride by a commercially available triglyceride measurement kit and the like.

In one embodiment, the present invention provides a culture method of mesenchymal stem cells, comprising a step of culturing mesenchymal stem cells in the medium of the present invention (hereinafter sometimes to be described as "the culture method of the present invention").

While a culture container to be used for the culture of mesenchymal stem cell is not particularly limited as long as mesenchymal stem cells can be cultured, a flask, tissue culture flask, dish, petri dish, tissue culture dish, multidish, microplate, microwell plate, multiplate, multiwell plate, microslide, chamber slide, Schale, tube, tray, culture bag and roller bottle can be mentioned.

The culture container may be cell adhesive or cell non-adhesive, and is appropriately selected according to the object. A cell adhesive culture container may be coated with any cell supporting substrate such as extracellular matrix (ECM) and the like, in an attempt to improve the adhesiveness of the culture container surface to a cell. The cell supporting substrate may be any substance aiming at adhesion of mesenchymal, and examples thereof include Matrigel, collagen, gelatin, poly-L-lysine, poly-D-lysine, laminin, fibronectin and the like.

Other culture conditions can be appropriately determined. For example, while the culture temperature is not particularly limited, it can be about 30 to 40° C., preferably about 37° C. The $CO_2$ concentration can be about 1 to 10%, preferably about 2 to 5%. The oxygen concentration can be 1 to 20%, preferably 1 to 10%.

In a preferable embodiment, the culture method of the present invention may further comprise a step of growing mesenchymal stem cells for not less than 50 days, preferably not less than 70 days, more preferably not less than 87 days, further preferably not less than 118 days. According to the culture method of the present invention, a large amount of mesenchymal stem cells can be obtained by culturing for a long period as mentioned above since the proliferative capacity of mesenchymal stem cell is not lost and, for example, mesenchymal stem cells in the number 1230 times or more larger than that at the start of the culture can be obtained.

The present invention also provides a cell composition obtained by the culture method of the present invention (hereinafter to be also described as "the cell composition of the present invention"). In the cell composition of the present invention, the majority (e.g., 60%, preferably 70%, more preferably 80%, further preferably 90%, most preferably 100% of the cells in the cell composition) is preferably undifferentiated mesenchymal stem cell. Examples of known marker of mesenchymal stem cell include CD73, CD90 and CD105. Therefore, in the cell composition of the present invention, the majority (e.g., 60%, preferably 70%, more preferably 80%, further preferably 90%, most preferably 100% of the cells in the cell composition) is preferably positive to any one, preferably a combination of any two, more preferably all 3 markers, of CD73, CD90 and CD105. More preferably, the cell composition of the present invention does not express a molecule not expressed by mesenchymal stem cells. Examples of the molecule not expressed by mesenchymal stem cell include CD45 (expressed by hematopoietic stem cell), CD34 (expressed by hematopoietic stem cell), CD14 (expressed by monocyte, macrophage), CD11b (expressed by monocyte, macrophage, NK cell, granulocyte), CD79 (expressed by B cell), CD19 (expressed by B cell) and HLA-DR (expressed by dendritic cell, B cell, monocyte, macrophage) and the like. In a preferable embodiment, therefore, in the cell composition of the present invention, the majority thereof (e.g., 60%, preferably 70%, more preferably 80%, further preferably 90%, most preferably 100% of the cells in the cell composition) is preferably negative to the expression of a molecule not expressed by mesenchymal stem cell.

The cells obtained by the culture method of the present invention can be preferably used for medical use such as cell medicine and the like. The cells can be used without differentiation or after differentiation into osteocyte, chondrocyte, adipocyte and the like, depending on the target disease and the like. Examples of the target disease include osteonecrosis of the lunate bone, avascular necrosis of the femoral head, osteochondritis disease, lumbar disc herniation, ischemic cardiac diseases, epidermolysis bullosa and the like. The cells can also be used for cosmetic surgery after differentiation into adipocytes.

Examples of the animal to be the subject of the cell medicine include experiment animals such as rodents (e.g., mouse, rat, hamster, guinea pig and the like), rabbit and the like, domestic animals such as swine, bovine, goat, horse, sheep, mink and the like, pets such as dog, cat and the like, primates such as human, monkey, Macaca mulatta, marmoset, orangutan, chimpanzee and the like, and the like, preferably human.

The dosage and administration method of cells in the above-described cell medicine are not particularly limited as long as the desired effect can be obtained, and can be appropriately determined according to the disease and the level of symptom to be the treatment target, animal to be the subject of administration and the like.

Other features of the invention will become apparent in the course of the following descriptions of exemplary embodiments which are given for illustration of the invention and are not intended to be limiting thereof.

EXAMPLES

Material and Methods.
1. Cells

Human mesenchymal stem cells collected and prepared from the normal human donor, which were purchased from LONZA (catalog No.: PT-2501), and human mesenchymal stem cells autonomously collected by the present inventors (lot Nos.: BM103-104) were used.

2. Culture of Mesenchymal Stem Cell

In the culture of mesenchymal stem cell, FBS (fetal bovine serum, Life Technologies Corporation: 26400-044) after removal of low molecules by dialysis was added to each of a medium composed of components (salts, vitamin and the like) constituting DMEM (Dulbecco's modified Eagle medium, GIBCO), which are other than amino acid (hereinafter sometimes to be indicated as "Zero medium"), such medium added with 20 kinds of amino acid (hereinafter sometimes to be indicated as "Full medium"), and such medium added with 13 kinds of amino acid excluding glycine, alanine, serine, proline, asparagine, aspartic acid and glutamic acid (hereinafter sometimes to be indicated as "−7 medium") to 10(v/v) % and used.

Table 1 shows the concentrations of the above-mentioned 7 kinds of amino acid in the serum used for culture after dialysis, the final concentrations of these amino acids during use when added to −7 medium, and the concentrations of these amino acids in a general medium.

TABLE 1

| | concentration in serum after dialysis (analyzed value) (μM) | concentration when added to −7 medium (calculated value) (μM) | concentration in general medium (DMEM/F12) (μM) |
| --- | --- | --- | --- |
| glycine | 8.67 | 0.7803 | 250 |
| alanine | 8.46 | 0.7614 | 50 |
| serine | 3.79 | 0.3411 | 250 |
| proline | 7.39 | 0.6651 | 150 |
| asparagine | 0.635 | 0.05715 | 50 |
| aspartic acid | 1.13 | 0.1017 | 50 |
| glutamic acid | 5.46 | 0.4914 | 50 |

Mesenchymal stem cells were cultured in an incubator at 37° C. under 5% $CO_2$ atmosphere.

3. Differentiation Culture into Adipocyte and Maintenance Culture of Adipocyte

Differentiation of mesenchymal stem cell into adipocyte was performed using a high glucose-containing DMEM medium (GIBCO) added with an adipose differentiation induction medium (10(v/v) % FBS (Life Technologies Corporation: 26400-044), 0.01 mg/mL insulin (Nacalai Tesque:

19251-95), 1 μM dexamethasone (Sigma Ltd.: D2915), 0.2 mM indomethacin (Sigma Ltd.: I7378), 0.5 mM isobutyl-methylxanthine (Sigma Ltd.: I7018)). The culture after differentiation into adipocyte was performed using a high glucose-containing DMEM medium (GIBCO) added with adipose maintenance medium (10(v/v) % FBS (Life Technologies Corporation: 26400-044), 0.01 mg/mL insulin (Nacalai Tesque: 19251-95)).

The differentiation culture of mesenchymal stem cell into adipocyte and the maintenance culture after differentiation were performed in an incubator at 37° C. under 5% $CO_2$ atmosphere.

4. Differentiation Induction into Adipocyte and Measurement of Differentiation Efficiency Mesenchymal stem cells were seeded at $2 \times 10^5$ cells per 1 well of a 6-well plate, and cultured in a medium for mesenchymal stem cells until the cells reached 100% confluence. The medium was exchanged with adipose differentiation induction medium and, after culture for 3 days, the medium was exchanged with adipose maintenance medium, and the cells were cultured for 3 more days. The culture in the adipose differentiation induction medium and the adipose maintenance medium for 6 days in total was repeated 3 cycles for 18 days in total.

The cells after the culture were fixed with 10% formalin, and subjected to Oil Red O staining. The cells were dissolved in 0.1% Thesit (registered trade mark) (lauromacrogol), and triglyceride level was quantified by a serum triglyceride measurement kit (Sigma Ltd.: TR0100-1KT). Protein was quantified using a BCA (bicinchonine acid) reagent and the differentiation efficiency of each cell was studied based on the comparison of the triglyceride level per protein amount.

Results

Figure 1:
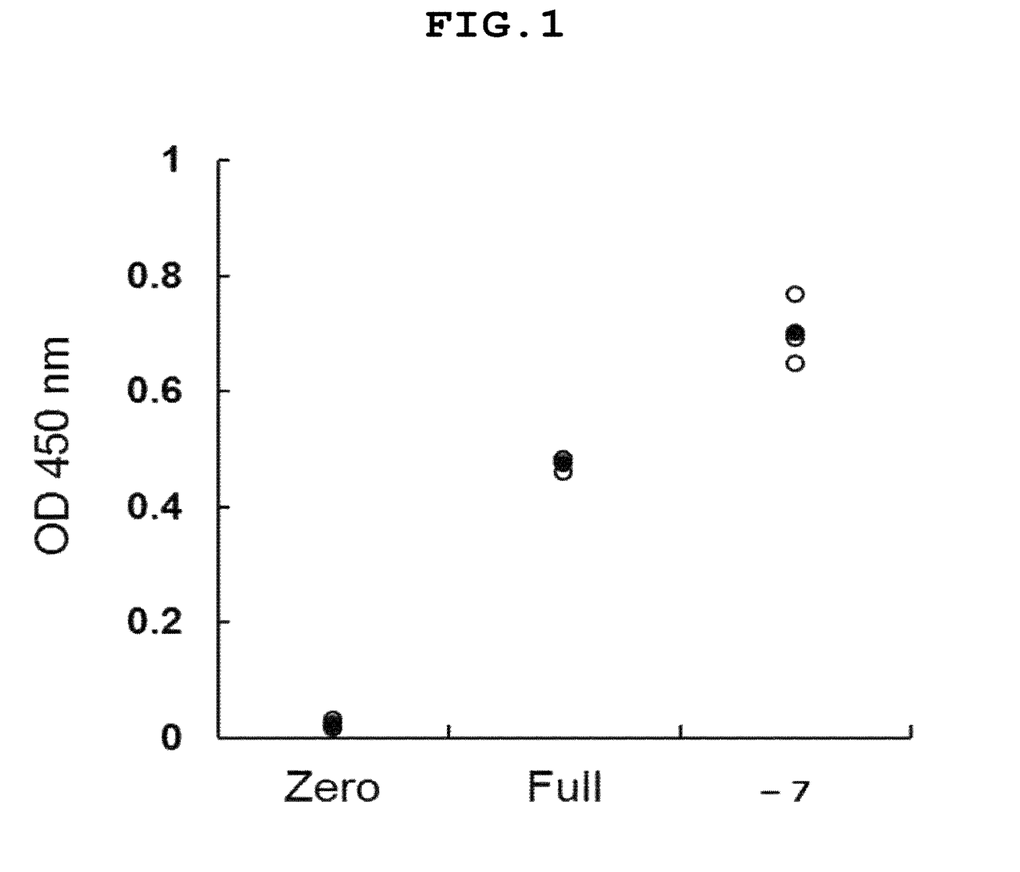
FIG. 1 shows a cell growth promoting effect on human mesenchymal stem cells (lot No.: OF3825) by 7 days of culture in the medium of the present invention.

Example 1: Cell Growth Promoting Effect on Mesenchymal Stem Cell by Short Period Culture in −7 Medium (FIG. 1)

Human mesenchymal stem cells (lot No.: OF3825) were cultured for 7 days in Zero medium, Full medium, or −7 medium, and the cell number was evaluated. Cell number was counted by CCK assay. Using cell counting kit-8 (Dojindo), which is a commercially available kit, the operation was performed according to the instruction manual attached to the kit. In CCK assay, the cell number was in proportion to OD450 nm (vertical axis). Each medium was evaluated with 3 wells, and the value of each well was shown with ○, and the mean of 3 wells was shown with ●. It was found that proliferation of mesenchymal stem cells was remarkably promoted in −7 medium as compared to culture in Full medium.

Figure 2:
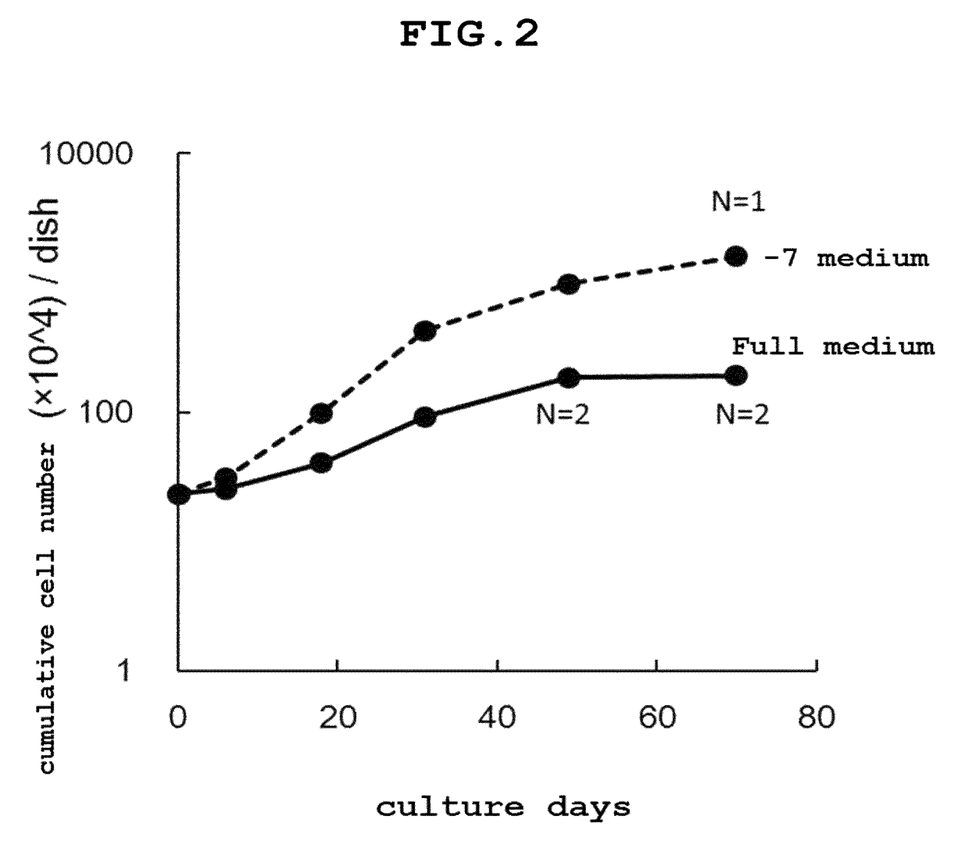
FIG. 2 shows a cell growth promoting effect on human mesenchymal stem cells (lot No.: OF3825) by about 70 days of culture in the medium of the present invention.

Example 2: Cell Growth Promoting Effect on Mesenchymal Stem Cell by Long-Period Culture in −7 Medium (FIG. 2)

Human mesenchymal stem cells (lot No.: OF3825) were cultured for 70 days in −7 medium or Full medium, and cumulative cell number when cultured in each medium was counted. At the time of passage, the cells were detached from the culture container by a trypsin treatment, mixed with Trypan Blue, the cell suspension was applied to a hemocytometer, and the cell number was counted. The cell number was counted by a similar method also in the following Examples. As compared to culture in Full medium, the cumulative cell number remarkably increased when cultured in −7 medium. Therefore, it was shown that −7 medium is a medium suitable for the growth culture of mesenchymal stem cells for a long period.

Figure 3:
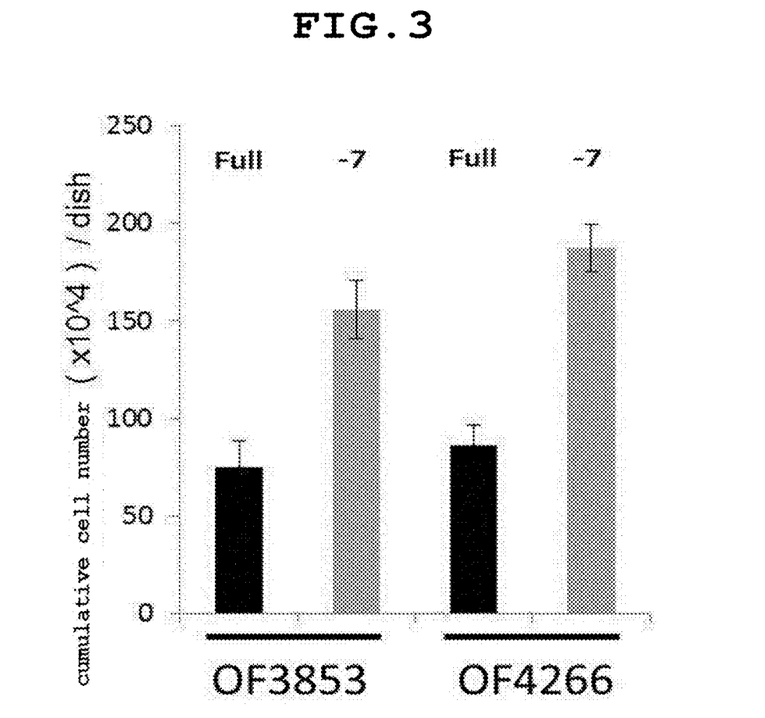
FIG. 3 shows a cell growth promoting effect on human mesenchymal stem cells (lot Nos.: OF3853 and OF4266) by about 30 days in the medium of the present invention.

Example 3: Cell Growth Promoting Effect on Different Lots of Mesenchymal Stem Cells by Culture in −7 Medium (FIG. 3)

Human mesenchymal stem cells (lot No.: OF3853 and lot No.: OF4266) were cultured for 30 days in −7 medium or Full medium, and the cumulative cell number was counted. The both lots of human mesenchymal stem cells showed a remarkable growth promoting effect by −7 medium.

Example 4: Consideration of Growth Culture Possible Period in Culture of Mesenchymal Stem Cells in Full Medium (Figure, FIG. 4)

Figure 4:
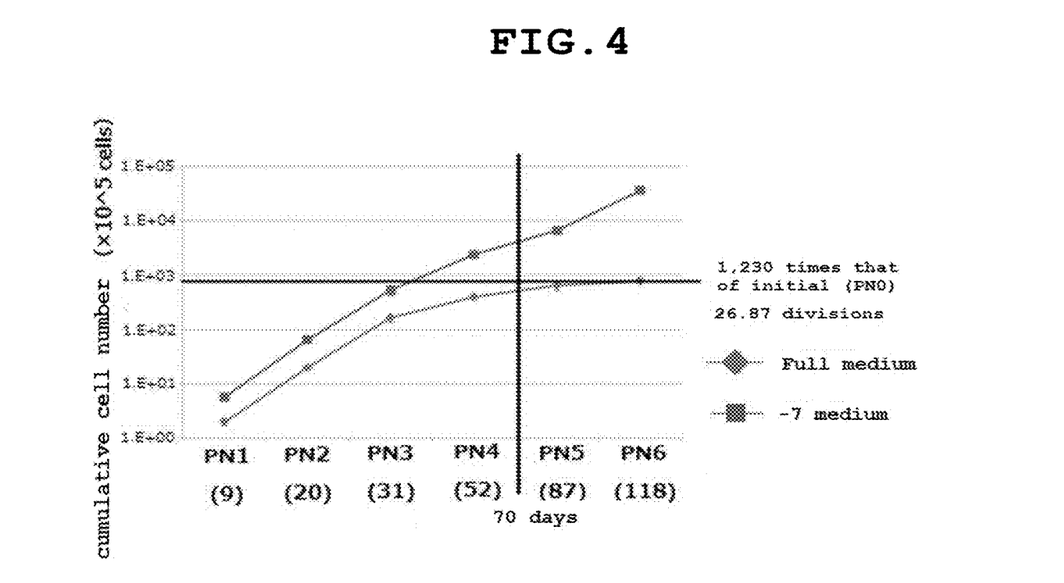
FIG. 4 shows a cell growth promoting effect on human mesenchymal stem cells (lot No.: BM103) by 109 days from the first passage in the medium of the present invention. The numbers in the parentheses on the horizontal axis show the number of days from the start of the culture.

Using −7 medium or Full medium, human mesenchymal stem cells (lot No.: BM103) were cultured for 109 days, and each cumulative cell number was counted. When cultured in −7 medium, the cumulative cell number continued to grow without stagnating, whereas when cultured in Full medium, the cumulative cell number has almost ceased to grow from day 70 from the start of the culture and thereafter. By the culture until cease of growth, the final cumulative cell number by culture in Full medium was 1230 times the cell number at the time of the start of the culture. Therefore, it was clarified that the possible period of growth culture of mesenchymal stem cells in Full medium is about 70 days, and the cumulative cell number in this case is about 1230 times the cell number at the time of the start of the culture.

Figure 5A:
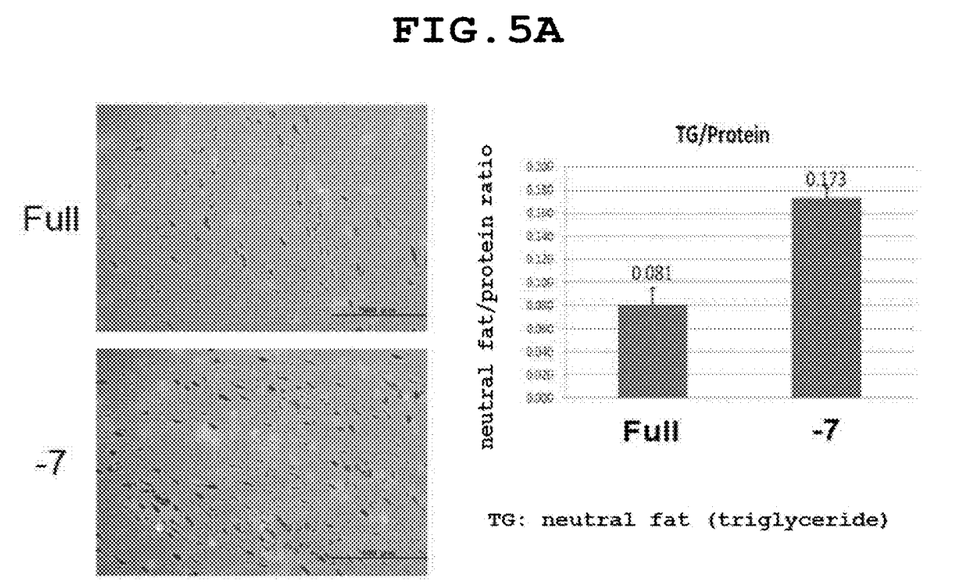
FIG. 5A and FIG. 5B show a differentiation promoting effect on human mesenchymal stem cell (lot No.: BM103PN2 (FIG. 5A) and BM105PN2 (FIG. 5B)) cultured in the medium of the present invention into adipocytes.
Figure 5B:
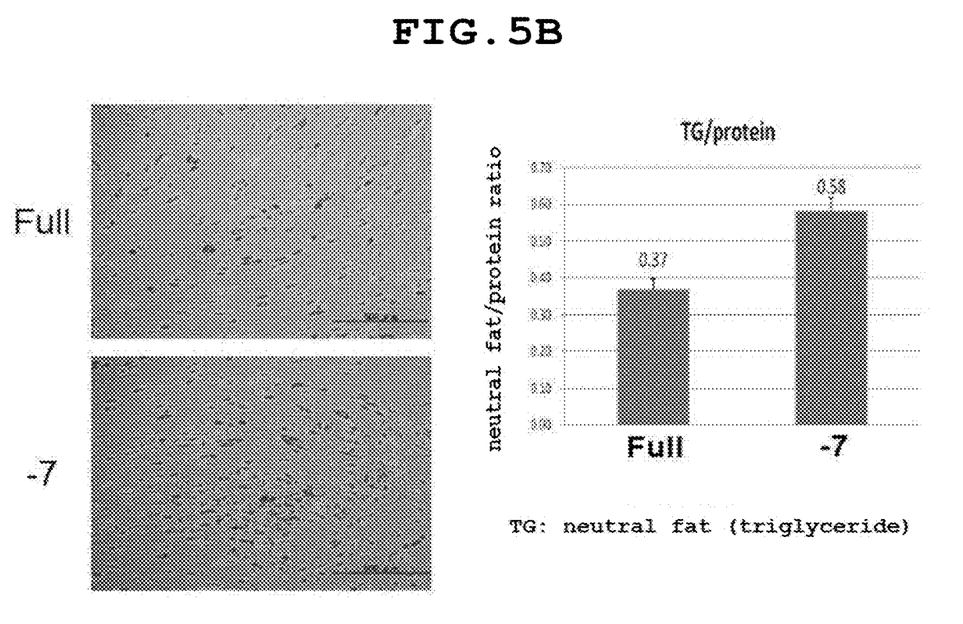

Reference Example 1: Promoted Differentiation of Mesenchymal Stem Cells Cultured in −7 Medium into Adipocytes (FIG. 5)

Using human mesenchymal stem cells (lot Nos.: BM103PN2 (FIG. 5A) and BM105PN2 (FIG. 5B)) cultured in −7 medium or Full medium for 20 to 24 days, differentiation into adipocyte, osteocyte or chondrocyte was induced. As for differentiation into osteocyte and chondrocyte, the mesenchymal stem cells cultured in −7 medium showed the same level of differentiation efficiency as compared to those cultured in Full medium. As for differentiation into adipocyte, the mesenchymal stem cells cultured in −7 medium showed remarkably high differentiation efficiency, as compared to those cultured in Full medium (FIG. 5A and FIG. 5B). Therefore, it was shown that −7 medium is a medium that enables differentiation into adipocyte with efficiency higher than that of a conventional medium while maintaining the same level of differentiation potency as a conventional medium, as for the differentiation of mesenchymal stem cells into osteocyte and chondrocyte.

INDUSTRIAL APPLICABILITY

According to the present invention, growth culture of mesenchymal stem cells can be performed for a long period without senescence thereof, and the invention is particularly useful when a large amount of mesenchymal stem cells are required. Mesenchymal stem cells cultured according to the present invention can be preferably used for applications such as cell medicine and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A culture medium comprising histidine, isoleucine, leucine, lysine, methionine, phenylalanine, threonine, tryptophan, valine, arginine, cysteine, glutamine, tyrosine, glycine, alanine, serine, proline, asparagine, aspartic acid, and glutamic acid,
wherein said culture medium comprises components constituting basal medium, which are other than amino acid,
wherein the concentrations of glycine, alanine, serine, proline, asparagine, aspartic acid, and glutamic acid in the culture medium are less than 5 µM, less than 5 µM, less than 3 µM, less than 5 µM, less than 1 µM, less than 2 µM, and less than 3 µM, respectively,
wherein the basal medium is selected from DMEM, IMDM (Iscove's Modified Dulbecco's Medium), GMEM (Glasglow's MEM), RPMI-1640, α-MEM, Ham's Medium F-12, Ham's Medium F-10, Ham's Medium F12K, Medium 199, ATCC-CRCM30, DM-160, DM-201, BME, Fischer, McCoy's 5A, Leibovitz's L-15, RITC80-7, MCDB105, MCDB107, MCDB131, MCDB153, MCDB201, NCTC109, NCTC135, Waymouth's MB752/1, CMRL-1066, Williams' medium E, Brinster's BMOC-3 Medium, and a mixed medium thereof.

2. The medium according to claim 1, wherein the concentrations of glycine, alanine, serine, proline, asparagine, aspartic acid, and glutamic acid are less than 1 µM, less than 1 µM, less than 0.7 µM, less than 1 µM, less than 0.1 µM, less than 0.5 µM, and less than 0.7 µM, respectively.

3. The medium according to claim 1, which is free of a component derived from a non-human animal.

4. A method of culturing a mesenchymal stem cell, comprising culturing a mesenchymal stem cell in a medium according to claim 1.

5. The method according to claim 4, wherein said mesenchymal stem cell is a human mesenchymal stem cell.

6. The method according to claim 5, wherein said culturing said mesenchymal stem cell comprises growing a mesenchymal stem cell for not less than 70 days.

7. The method according to claim 5, wherein the mesenchymal stem cell is collected from bone marrow.

8. A cell composition, comprising a mesenchymal stem cell and a medium according to claim 1.

9. The cell composition according to claim 8, wherein the mesenchymal stem cell is positive to at least one marker selected from the group consisting of CD73, CD90, and CD105.

10. The cell composition according to claim 8, wherein the mesenchymal stem cell is positive to at least one marker selected from the group consisting of CD73, CD90, and CD105, and negative to CD45, CD34, CD14, CD11 b, CD79, CD19 and HLA-DR.

* * * * *